US00PP27613P3

(12) United States Plant Patent
O'Connell

(10) Patent No.: US PP27,613 P3
(45) Date of Patent: Jan. 24, 2017

(54) ***AEONIUM* PLANT NAMED 'EMERALD ICE'**

(50) Latin Name: ***Aeonium* hybrid**
Varietal Denomination: Emerald Ice

(71) Applicant: Renee O'Connell, Escondido, CA (US)

(72) Inventor: Renee O'Connell, Escondido, CA (US)

(73) Assignee: Altman Plants, Vista, CA (US)

( * ) Notice: Subject to any disclaimer, the term of this patent is extended or adjusted under 35 U.S.C. 154(b) by 40 days.

(21) Appl. No.: 14/544,901

(22) Filed: Mar. 6, 2015

(65) Prior Publication Data

US 2016/0270280 P1 Sep. 15, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen Redden

(57) ABSTRACT

A new and distinct *Aeonium* cultivar named 'Emerald Ice' is disclosed, characterized by very even, concentric rosettes, comprised of an abundance of green leaves, colored marginally with creamy white, and arranged in an attractive, variegated geometric pattern. Further, the new cultivar 'Emerald Ice' freely offsets, enabling increased and faster propagation of the cultivar. In addition, the robust growth, in combination with the freely offsetting characteristic of the new cultivar 'Emerald Ice', results in the clusters at an early age, and enhances production intervals. The new variety is an *Aeonium*, part of the Crassulaceae complex that includes *Aeonium, Echeveria, Graptopetalum, Sedum* and others. *Aeonium* is a popular genus, typically produced as container plants for the patio or as landscape plants.

2 Drawing Sheets

Figure 1:
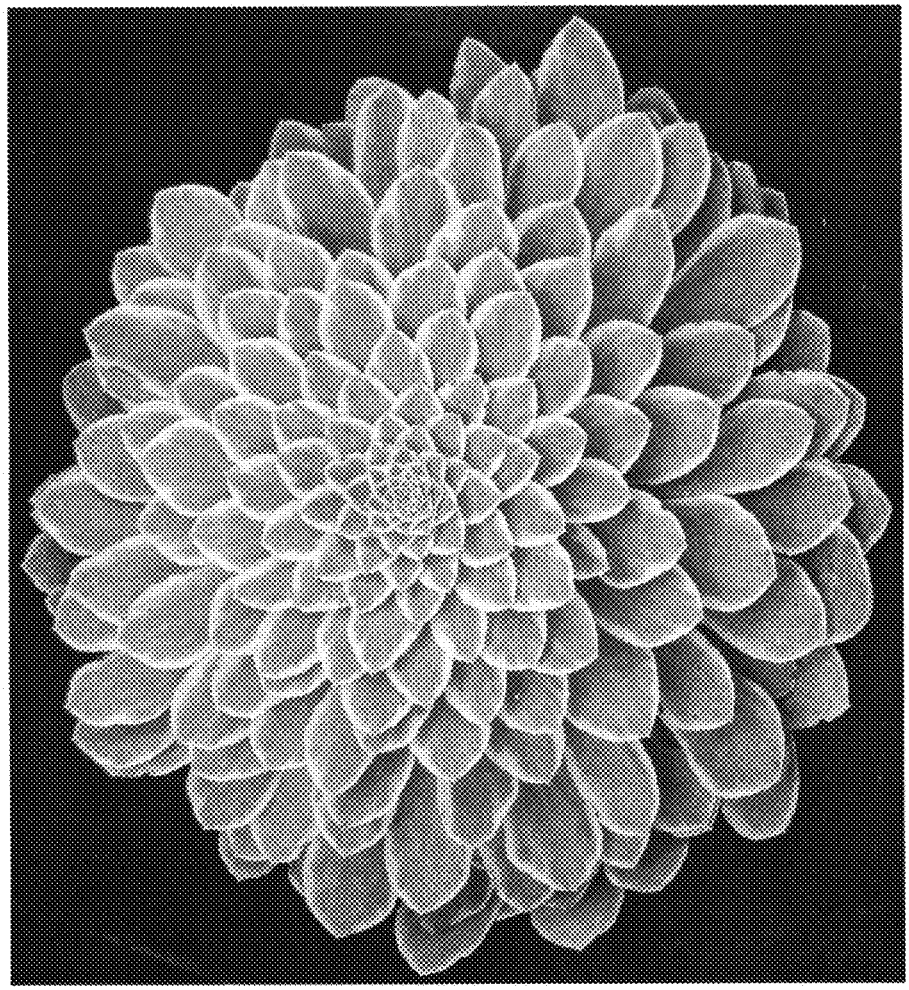

Latin name of the genus and species: *Aeonium* hybrid.
Variety denomination: 'EMERALD ICE'.

BACKGROUND OF THE INVENTION

The new cultivar, *Aeonium* 'Emerald Ice', was found by the inventor, Renee O'Connell, as a naturally occurring, whole plant, mutation in an existing population of the unpatented variety *Aeonium* hybrid 'Party Platter'. The parent variety is the product is a planned breeding program conducted same inventor, Renee O'Connell. *Aeonium* 'Emerald Ice' was discovered by the inventor, Renee O Connell, in November of 2011, in a block of motherstock plants of *Aeonium* 'Party Platter' at a commercial greenhouse in Vista. Calif.

Asexual reproduction of the new cultivar 'Emerald Ice' was first performed in Vista, Calif., at a commercial greenhouse, by vegetative cuttings in December of 2011. 'Emerald Ice' has since produced multiple generations and has shown that the unique features of this cultivar are stable and reproduced true to type.

SUMMARY OF THE INVENTION

The cultivar 'EMERALD ICE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EMERALD ICE' These characteristics in combination distinguish 'EMERALD ICE' as a new and distinct *Aeonium* cultivar:

1. Displays a low growing morphology, in combination with variegation, not exhibited by other known *Aeonium* cultivars.
2. Exhibits very concentric, flattened rosettes with an abundance of leaves, combining with the variegation to create an unusual geometric pattern, not displayed by comparable *Aeonium* cultivars.
3. Freely offsetting, forming low growing clusters quickly, a growth habit not displayed by comparable *Aeonium* cultivars.
4. Easily and rapidly propagated due to robust growth, and prolific offsetting, as compared with other *Aeonium* cultivars.

Plants of the new cultivar 'EMERALD ICE' are similar to plants of the parent, *Aeonium* 'Party Platter' in most horticultural characteristics, however, plants of the new cultivar 'EMERALD ICE' differ in the following;

1. Displays a green and creamy white variegation, displaying leaves of multiple green shades accented by creamy white margins; foliage of *Aeonium* 'Party Platter' is not variegated.
2. Forms rosettes that are of more compact morphology than the rosettes of *Aeonium* 'Party Platter'.
3. Exhibits a more geometric appearance than that of *Aeonium* 'Party Platter', as a result of the more compact rosette in combination with the attractive variegation.

COMMERCIAL COMPARISON

Plants of the new cultivar 'EMERALD ICE' are comparable to the unpatented, commercial variety *Aeonium arboreum* 'Tricolor'. The two *Aeonium* varieties are similar in most horticultural characteristics; however, the new variety 'EMERALD ICE' differs in the following:

1. Displays a more geometric variegation than does *Aeonium arboreum* 'Tricolor'.
2. Forms a more evenly concentric rosette than does *Aeonium arboreum* 'Tricolor', producing a more uniform rosette plant form.
3. Produces a rosette with an abundance of leaves, creating a plant with a much more full appearance, than does *Aeonium arboreum* 'Tricolor'
4. Offsets more profusely than *Aeonium arboreum* 'Tricolor', enhancing the propagation rate, and producing a morphologically aesthetic cluster.

Plants of the new cultivar 'EMERALD ICE' can also be comparable to the unpatented commercial variety *Aeonium* 'Sunburst'. The two *Aeonium* varieties are similar in most horticultural characteristics; however, the new variety 'EMERALD ICE' differs in the following:

1. Displays a more geometric variegation than does *Aeonium* 'Sunburst.
2. Forms a more evenly concentric rosette than does *Aeonium* 'Sunburst', producing a more uniform rosette plant form.
3. Produces a rosette with an abundance of leaves, creating a plant with a much more full appearance, than does *Aeonium* 'Sunburst'.
4. Offsets more profusely than does *Aeonium* 'Sunburst', enhancing the propagation rate, and producing a morphologically aesthetic cluster.

BRIEF DESCRIPTION OF THE PHOTOGRAPHS

The accompanying photograph in FIG. 1 illustrates in full color the top view of a rosette typical of plants of *Aeonium* 'Emerald Ice' grown in a greenhouse in Vista, Calif.

Figure 2:
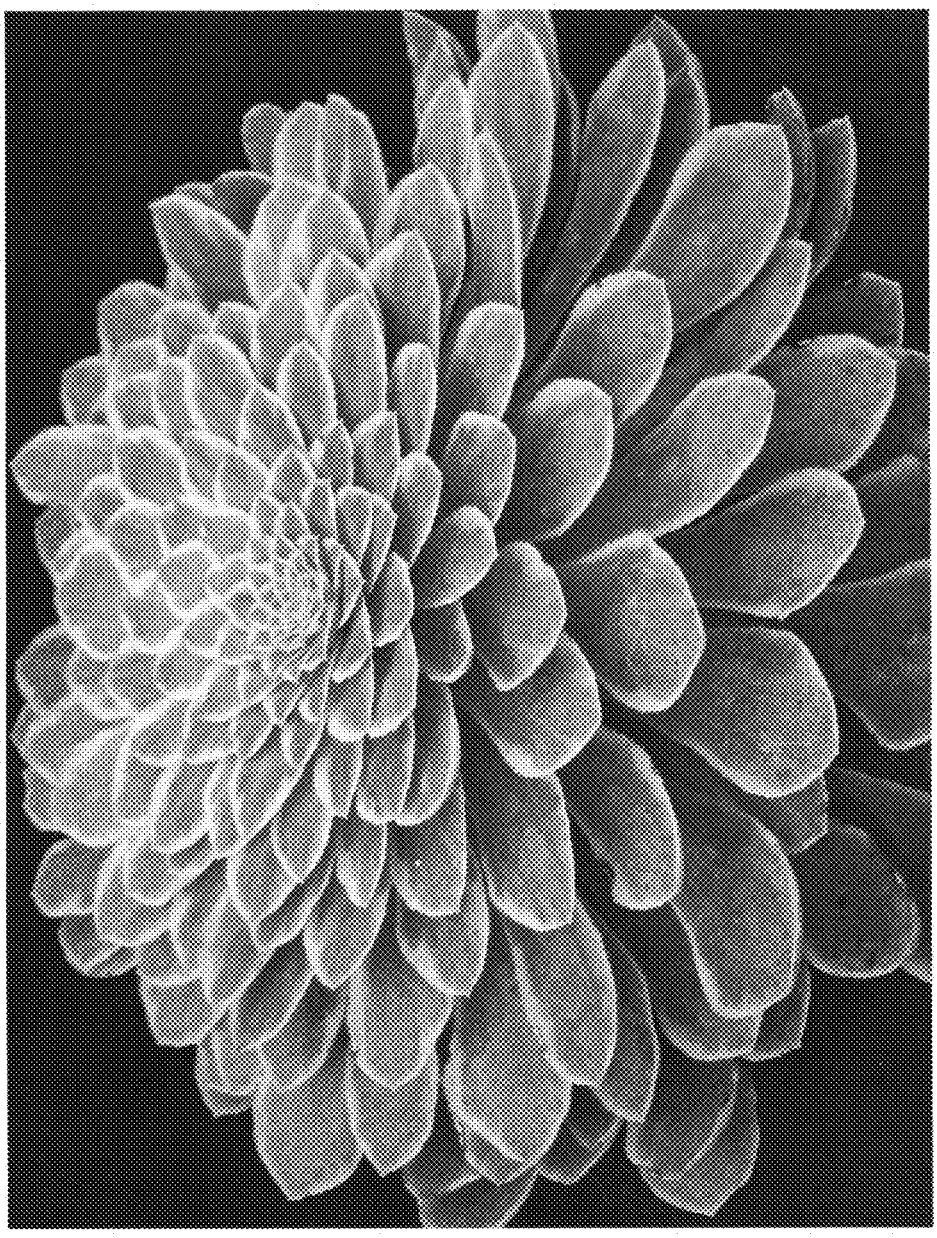

FIG. 2 illustrates in full color the side view of a rosette typical of plants of *Aeonium* 'Emerald Ice' as grown in a commercial greenhouse in Vista. Age of the plant photographed is approximately 14 weeks from a rooted plantlet.

The photographs were taken using conventional techniques and although colors may appear different from actual colors due to light reflectance it is as accurate as possible by conventional photographic techniques. All photographs provided by the breeder.

DETAILED BOTANICAL DESCRIPTION

In the following description, color references are made to the Pantone Process Color System Guide, Pantone CYMK, 2014, except where general terms of ordinary dictionary significance are used. The following observations and measurements describe 'Emerald Ice' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Aeonium* hybrid 'EMERALD ICE'.

PROPAGATION

Type of propagation typically used: Terminal vegetative divisions.

Time to initiate roots: About 18 days at approximately 24° C.

Root description: Fibrous.

PLANT

Age of plant described: Approximately 4 months.

Container size of the plant described: 20.5 cm.

Growth habit: Upright, caulescent, with a terminal rosette, freely offsetting from below rosette and between leaves of the rosette to produce cluster.

Height: Approximately 14 cm to top of highest leaf. Height in cm to top of inflorescence is unknown as plant has been undergoing propagation, and has not yet flowered.

Plant spread: 23 cm.

Growth rate: Moderately fast.

Branching characteristics: Freely offsetting.

FOLIAGE

Leaf:

*Arrangement*.—Rosulate.

*Average length*.—Approximately 8 cm.

*Longest length*.—Approximately 11.3 cm.

*Widest width*.—Approximately 1.35 cm.

*Width at base*.—0.7 cm.

*Shape of blade*.—Oblanceolate.

*Apex*.—Acuminate.

*Base*.—Cuneate.

*Margin*.—Ciliate.

*Texture of top surface*.—Glabrous.

*Texture of bottom surface*.—Glabrous.

*Quantity of leaves per plant*.—Approximately 190.

*Color*.—Young foliage upper side: Near P 159-15 U Pantone & P 159-16 U Pantone. Young foliage, upper side, apical margin: Near P 166-3 U Pantone. Young foliage upper side, near base: Near P 160-9 U Pantone. Young foliage, upper side, basal margin: Near P 160-5 U Pantone. Young foliage, under side: Near P 159-15 U Pantone & P 159-16 U Pantone. Mature foliage upper side: Near P 159-15 U Pantone & P 159-6 U Pantone. Mature foliage, under side: Near P 159-15 U Pantone & P 159-6 U Pantone. Mature foliage, under side, apical margin: Near P 166-3 U Pantone. Mature foliage, under side, near stem: Near P 160-11 U Pantone.

*Venation*.—There is no visual appearance of venation.

FLOWER

Flowering not observed to date.

REPRODUCTIVE ORGANS

Flowering not observed to date.

OTHER CHARACTERISTICS

Fruits and seeds: Plant has not flowered to date.

Temperature tolerance: Tolerates temperatures from approximately −2 degrees C. to 32 degrees C.

Disease/pest resistance: Displays the same disease and pest resistance of any other comparable *Aeonium*.

Drought tolerance: Tolerates at least 3 weeks of high temperatures without supplemental water, showing no serious damage to plant.

What is claimed is:

1. A new and distinct cultivar of *Aeonium* plant named 'EMERALD ICE' as herein illustrated and described.

* * * * *